United States Patent
Joye et al.

(12)

(10) Patent No.: US 7,060,062 B2
(45) Date of Patent: Jun. 13, 2006

(54) CONTROLLABLE PRESSURE CRYOGENIC BALLOON TREATMENT SYSTEM AND METHOD

(75) Inventors: James Joye, Saratoga, CA (US); Richard S. Williams, Redwood City, CA (US); Glen Reuschling, Watsonville, CA (US)

(73) Assignee: Cryo Vascular Systems, Inc., Los Gatos, CA (US)

( * ) Notice: Subject to any disclaimer, the term of this patent is extended or adjusted under 35 U.S.C. 154(b) by 138 days.

(21) Appl. No.: 10/455,253

(22) Filed: Jun. 4, 2003

(65) Prior Publication Data

US 2005/0038421 A1 Feb. 17, 2005

(51) Int. Cl.
*A61B 18/18* (2006.01)

(52) U.S. Cl. .................................................. 606/21

(58) Field of Classification Search .......... 606/20–26
See application file for complete search history.

(56) References Cited

U.S. PATENT DOCUMENTS

| | | | |
|---|---|---|---|
| 3,125,096 A | 3/1964 | Antiles et al. |
| 3,901,241 A | 8/1975 | Allen, Jr. |
| 4,336,691 A | 6/1982 | Burstein et al. |
| 4,754,752 A | 7/1988 | Ginsburg et al. |
| 5,019,075 A | 5/1991 | Spears et al. |
| 5,041,089 A | 8/1991 | Mueller et al. |
| 5,078,713 A | 1/1992 | Varney |
| 5,092,841 A | 3/1992 | Spears |
| 5,106,360 A | 4/1992 | Ishiwara et al. |
| 5,147,355 A | 9/1992 | Friedman et al. |
| 5,151,100 A | 9/1992 | Abele et al. |
| 5,190,539 A | 3/1993 | Fletcher et al. |
| 5,191,883 A | 3/1993 | Lennox et al. |
| 5,196,024 A | 3/1993 | Barath |
| 5,275,595 A | 1/1994 | Dobak, III |
| 5,458,612 A | 10/1995 | Chin |
| 5,486,208 A | 1/1996 | Ginsburg |
| 5,501,681 A | 3/1996 | Neuwirth et al. |
| 5,545,195 A | 8/1996 | Lennox et al. |
| 5,617,739 A | 4/1997 | Little |
| 5,624,392 A | 4/1997 | Saab |
| 5,644,502 A | 7/1997 | Little |
| 5,733,280 A | 3/1998 | Avitall |

(Continued)

FOREIGN PATENT DOCUMENTS

WO      WO 91/05528      5/1991

(Continued)

OTHER PUBLICATIONS

Gage, M.D., Andrew A., et al., "Freezing injury to large blood vessels in dogs," Surgery, vol. 61, No. 5, May, 1997, pp. 748-754.

*Primary Examiner*—Michael Peffley
(74) *Attorney, Agent, or Firm*—Townsend and Townsend and Crew LLP.

(57) ABSTRACT

Devices, systems, and methods controllably cool blood vessels and other body lumens. The blood vessel will often be treated for atherosclerotic or other diseases by inflating a balloon so as to engage the surrounding luminal wall. Controlled cooling of the balloon effected by a change in phase of a cryogenic fluid within the balloon typically a change from a liquid phase to a gas phase can be provided with a controlled, gradual inflation of the balloon. A single control system can be used for any of a variety of alternative selectable balloon catheters having significantly differing cooling fluid flow characteristics.

31 Claims, 7 Drawing Sheets

U.S. PATENT DOCUMENTS

| | | |
|---|---|---|
| 5,868,735 A | 2/1999 | Lafontaine |
| 5,902,299 A | 5/1999 | Jayaraman |
| 6,283,959 B1 * | 9/2001 | Lalonde et al. ............... 606/21 |
| 6,355,029 B1 * | 3/2002 | Joye et al. .................... 606/21 |
| 6,428,534 B1 * | 8/2002 | Joye et al. .................... 606/21 |
| 6,551,274 B1 * | 4/2003 | Heiner ....................... 604/113 |
| 6,575,966 B1 * | 6/2003 | Lane et al. .................... 606/21 |
| 6,786,901 B1 * | 9/2004 | Joye et al. .................... 606/21 |
| 2002/0198558 A1 * | 12/2002 | Briscoe et al. ............. 606/192 |

FOREIGN PATENT DOCUMENTS

WO  WO 98/38934  9/1998

* cited by examiner

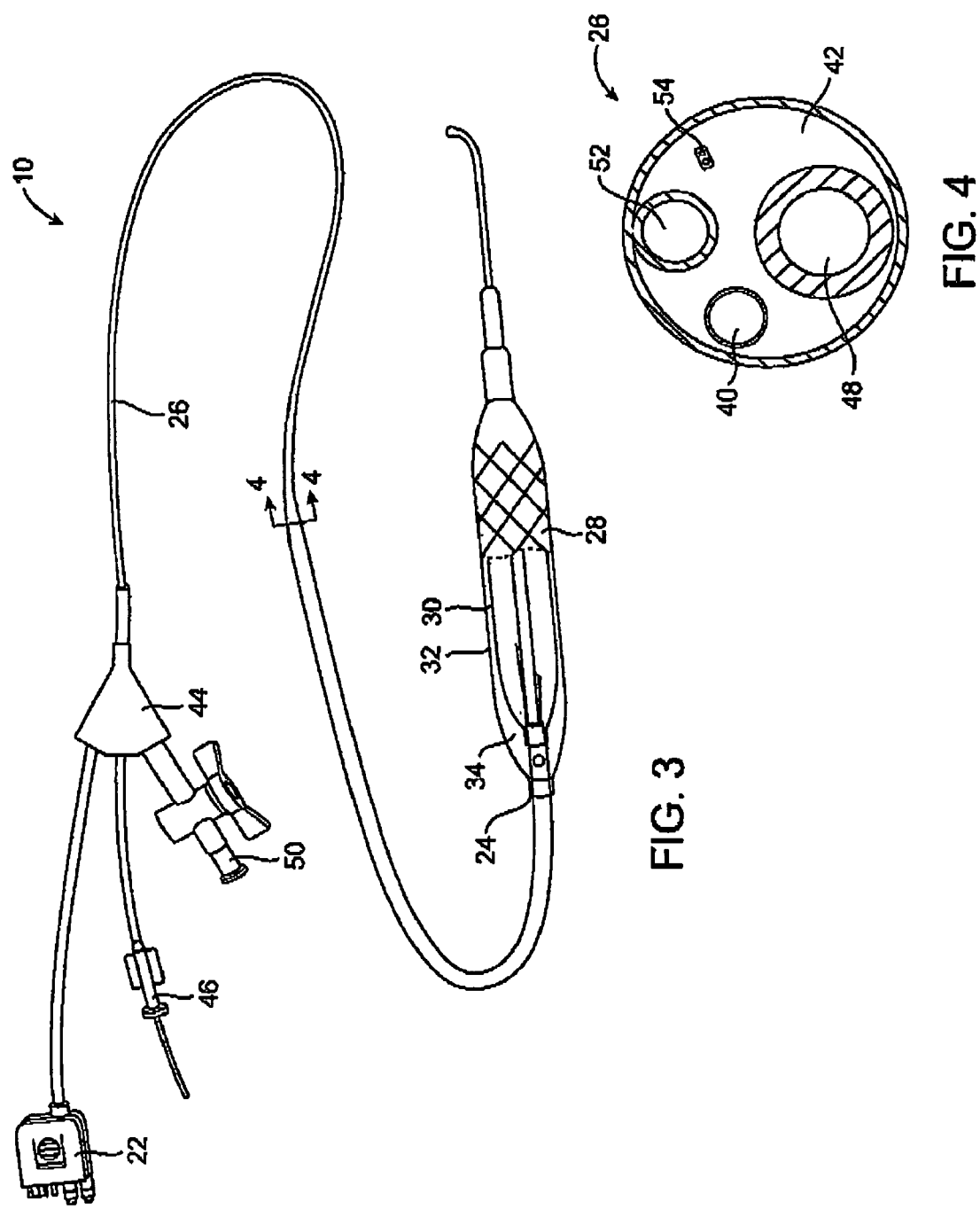

CONTROLLABLE PRESSURE CRYOGENIC BALLOON TREATMENT SYSTEM AND METHOD

BACKGROUND OF THE INVENTION

The present invention relates generally to apparatus and methods for treatment of blood vessels using cooling. More particularly, the invention provides systems, devices, and methods for cryogenically treating a lesion within a patient's vasculature while controlling the pressure state of a cooling balloon.

A number of percutaneous intravascular procedures have been developed for treating atherosclerotic disease in a patient's vasculature. The most successful of these treatments is percutaneous transluminal angioplasty (PTA). PTA employs a catheter having an expansible distal end, usually in the form of an inflatable balloon, to dilate a stenotic region in the vasculature to restore adequate blood flow beyond the stenosis. Other procedures for opening stenotic regions include directional atherectomy, rotational atherectomy, laser angioplasty, stents and the like. While these procedures, particularly PTA and stenting, have gained wide acceptance, they continue to suffer from the subsequent occurrence of restenosis.

Restenosis refers to the re-narrowing of an artery following an initially successful angioplasty or other primary treatment. Restenosis typically occurs within weeks or months of the primary procedure, and may affect up to 50% of all angioplasty patients to some extent. Restenosis results at least in part from smooth muscle cell proliferation in response to the injury caused by the primary treatment. This cell proliferation is referred to as "hyperplasia." Blood vessels in which significant restenosis occurs will typically require further treatment.

A number of strategies have been proposed to treat hyperplasia and reduce restenosis. Previously proposed strategies include prolonged balloon inflation, treatment of the blood vessel with a heated balloon, treatment of the blood vessel with radiation, the administration of anti-thrombotic drugs following the primary treatment, stenting of the region following the primary treatment, and the like. While these proposals have enjoyed varying levels of success, not one of these procedures is proven to be entirely successful in avoiding all occurrences of restenosis and hyperplasia.

It has recently been proposed to prevent or slow reclosure of a lesion following angioplasty by remodeling the lesion using a combination of dilation and cryogenic cooling. Co-pending U.S. patent application Ser. No. 09/203,011, filed Dec. 1, 1998 now U.S. Pat. No. 6,355,029, the full disclosure of which is incorporated herein by reference, describes an exemplary stmcture and method for inhibiting restenosis using a cryogenically cooled balloon. While these proposals show great promise for endovascular use, the described structures and methods for carrying out endovascular cryogenic cooling would benefit from still further improvements. In particular, work in connection with the present invention indicates that accurate control over balloon temperature, balloon inflation pressure, and the process of going from an uninflated balloon to an inflated cooling balloon may provide improved results. In general, enhanced control over temperatures, pressures, and the balloon inflation before or aller process during cryogenic cooling would be advantageous.

For these reasons, it would be desirable to provide improved devices, systems, and methods for cryogenic cooling of blood vessels and other body lumens. It would be particularly desirable if these improved devices, systems, and methods were capable of delivering treatment in a very controlled manner so as to limit injury of the adjacent tissues.

BRIEF SUMMARY OF THE INVENTION

The present invention provides improved devices, systems, and methods for controllably cooling blood vessels and other body lumens. The blood vessel will often be treated for atherosclerotic or other diseases by inflating a balloon so as to engage the surrounding luminal wall. Controlled cooling of the balloon may be effected by a change in phase of a cryogenic fluid within the balloon typically a change from a liquid phase to a gas phase. Selected treatment pressures may be provided while cooling temperatures remain within a selected range, and an intermediate state of the balloon (between a small profile uninflated configuration suitable for insertion and positioning, and a fully inflated configuration at the desired pressure and temperature) can be controlled. Advantageously, a controlled, gradual inflation of the balloon (by controlling a rate of change of the pressure within the balloon by "stair-step" increases in pressure, and the like) may inhibit injury. Despite a coupling of cryogenic cooling induced by changes from the liquid phase to the gas phase and the pressure environment within the balloon, controlled inflation can be effected by a single control system for any of a variety of alternative selectable balloon catheters having significantly differing cooling fluid flow characteristics.

In a first aspect, the invention provides a method for treating a region of a blood vessel. The method comprises positioning a balloon of a balloon catheter within the blood vessel and adjacent the region while the balloon is in a first configuration. The region is cooled with the balloon in a second configuration by changing a cooling fluid from a liquid phase to a gas phase within the balloon so as to urge the balloon radially outwardly. An intermediate cooling fluid pressure state within the balloon is controlled while the balloon is between the first configuration and the second configuration.

In many embodiments, the intermediate pressure state will comprise a rate of change of pressure within the balloon between the first configuration and the second configuration. This control may result in an inflation time from the first configuration to the second figuration of 0.25 seconds or more. The rate of change of pressure may be defined by a plurality of step increases in pressure within the balloon. The balloon catheter may be selected from among a plurality of differing alternative balloon catheters having differing cooling fluid flow characteristics. The cooling fluid pressure state may be controlled so as to compensate for the alternative cooling fluid flow characteristics, and provide the pressure change rate within a desired range.

The intermediate state may comprise an intermediate balloon pressure. The intermediate pressure may be greater than a first configuration balloon pressure and less than a second configuration balloon pressure. A cooling fluid supply may be coupled to a supply lumen of the balloon catheter so as to provide a fluid path extending from the fluid supply, distally along the supply lumen, into the balloon, and proximally along an exhaust lumen of the balloon catheter. The pressure may be controlled by venting at least a portion of the cooling fluid upstream of the balloon. Optionally, the pressure may be controlled by periodic opening and closing of a vent valve coupled to the fluid path upstream of the balloon. A fluid delivery valve may also be periodically opened and closed, with the fluid delivery valve being disposed along the fluid path between the fluid supply and the balloon. The cooling fluid may comprise, for example, nitrous oxide, and the vent valve may open and close according to a valve cycle time. The fluid delivery valve may open and close according to the valve cycle time, but the vent valve may be opened for a longer portion of the valve cycle time than the fluid delivery valve. A pressure may be sensed downstream of the balloon, and that sensed pressure may be used to determine the venting regime for the cooling fluid. In many embodiments, pressure sensed at or down stream of the balloon may be used by an exhaust pressure relief valve, optionally in combination with cycling of a vent valve and delivery valve.

The balloon catheter may be selected from among a plurality of differing alternative balloon catheters having differing alternative cooling fluid flow characteristics. The characteristics of the selected balloon catheter may determine a cooling fluid valve control regimen. The control regimen can provide a balloon temperature within a desired range, and alternative different control regimens may compensate for the different flow characteristics of the alternative balloon catheters. The flow characteristics of the selected balloon catheter may be determined by introducing an initial for calibration cooling fluid flow into the selected balloon catheter, and by sensing an exhaust flow property of the initial fluid flow from the balloon catheter.

In another aspect, the invention provides a method for cooling a region of a blood vessel to a predetermined cooling temperature range. The method comprises positioning a balloon of a balloon catheter system within the blood vessel and adjacent the region while the balloon is in a first configuration. A balloon inflation pressure is selected, and the balloon is inflated to the selected pressure by changing a cooling fluid from a liquid phase to a gas phase along a cooling fluid path of the balloon catheter system. The cooling fluid flow along the cooling fluid path is controlled so as to provide the selected balloon inflation pressure and the predetermined cooling temperature range.

Optionally, the pressure may be selected by selecting between a first pressure relief valve and a second pressure relief valve downstream of the balloon along the cooling fluid path. A lower pressure valve may be selected by opening the cooling fluid path to that lower pressure relief valve while the higher pressure relief valve remains coupled to the cooling fluid path.

In another aspect, the invention provides a catheter system for cooling a region of the blood vessel. The system comprises a balloon catheter having a catheter body with a proximal end, a distal end, and a balloon disposed near the distal end. The catheter body has a supply lumen and an exhaust lumen in fluid communication with the balloon. A fluid supply coupleable to the proximal end of the catheter body will define a cooling fluid path extending distally along the supply lumen, through the balloon, and returning proximally along the exhaust lumen. The fluid supply has a cooling fluid which changes phase from a liquid to a gas to effect cooling. A cooling fluid control system is coupled to the fluid path. The fluid control system has a first configuration in which the balloon is uninflated. A second configuration of the cooling fluid system results in a balloon inflation to a treatment pressure and cools the region to a treatment temperature. An intermediate configuration of the cooling fluid control system, results in a controlled intermediate pressure state of the balloon.

The intermediate pressure state may comprise a lower pressure than the treatment pressure. The intermediate pressure state may comprise a rate of change of the balloon inflation pressure. The pressure change rate may be such that inflation of the balloon from the first configuration to the second configuration may take over 1 second, often taking at least about 7 seconds or more. The cooling fluid may comprise nitrous oxide, and the treatment pressure may be in a range from about 7 to about 11 atms. Optionally, the pressure change rate may defined by a plurality of increasing pressure steps.

A plurality of alternative selectable balloon catheters having differing cooling fluid flow characteristics may be provided. Each alternative balloon catheter may be coupled to the fluid supply so as to define an associated alternative fluid path. The fluid control system can compensate for the differing flow characteristics so as to provide a treatment temperature in a desired temperature range, a treatment pressure in a desired treatment pressure range, and/or a pressure change rate in a desired pressure change rate range.

The flow control system may comprise a vent valve disposed along the cooling fluid path upstream of the balloon. A timer may be adapted for periodically cycling the vent valve open and closed. The flow control system may further comprise a fluid delivery valve disposed between the fluid supply and the balloon. The cooling fluid may comprise nitrous oxide, and the timer may periodically cycle the vent valve open and closed with a cycling time. The timer may also periodically cycle the fluid delivery valve open and closed with the same cycle of time period. The vent valve may, however, be opened for a larger portion of the cycle time period than the fluid delivery valve.

The flow control system may introduce an initial or calibrating cooling fluid flow into the balloon catheter, and may determine an appropriate cooling fluid regime in response to a characteristic of the initial flow downstream of the balloon. The cooling fluid flow regime may comprise a valve cycle period, and the downstream characteristic may comprise an exhaust pressure. The flow control system may comprise alternative selectable pressure relief valves downstream of the balloon.

In yet another aspect, the invention provides a catheter system for cooling a region of a blood vessel. The system comprises first and second alternatively selectable balloon catheters. Each balloon catheter has a catheter body with a proximal end, a distal end and a balloon disposed near the distal end. The catheter body has a supply lumen and an exhaust lumen in fluid communication with the balloon. A fluid supply is selectively couplable to the proximal end of each catheter body so as to define a cooling fluid path associated with the selected balloon catheter. The fluid supply has a cooling fluid which changes phase from a liquid to a gas so as to effect cooling. A characteristic of the first cooling fluid path associated with the first balloon catheter differs significantly from a second cooling fluid path associated with the second balloon catheter.

BRIEF DESCRIPTION OF THE DRAWINGS

FIG. 3 is a partial cutaway view of a balloon catheter of the system of FIG. 1.

FIG. 4 is a cross-sectional view through the balloon catheter of FIG. 3 taken along lines 4—4.

DETAILED DESCRIPTION OF THE INVENTION

The present invention generally provides improved devices, systems, and methods for cooling treatments of the luminal wall in body lumens and other tissues of the body. The invention often makes use of a balloon which is inflated by a cooling fluid so as to radially engage a vessel wall (or other surrounding tissue). The cooling fluid will often change from a first phase to a second phase at least in part within the balloon, so that the latent heat of vaporization cools the surrounding tissues. As introduction of suitable cooling fluids is capable of very rapidly expanding the balloon once the cooling fluid begins to boil from a liquid to a gas phase (often occurring soon after the fluid enters the catheter), the invention is capable of providing an advantageous control over the balloon inflation process. Specifically, an intermediate pressure state within the balloon, typically an intermediate pressure or an intermediate rate of change in pressure, may be controlled while the balloon is between a deflated configuration (suitable for insertion and positioning of the balloon) and a fully inflated configuration (at which a desired combination of temperature and pressure within the balloon can induce both luminal surface cooling and tissue dilation, balloon/ targeted tissue engagement, and/or the like).

Figure 1:
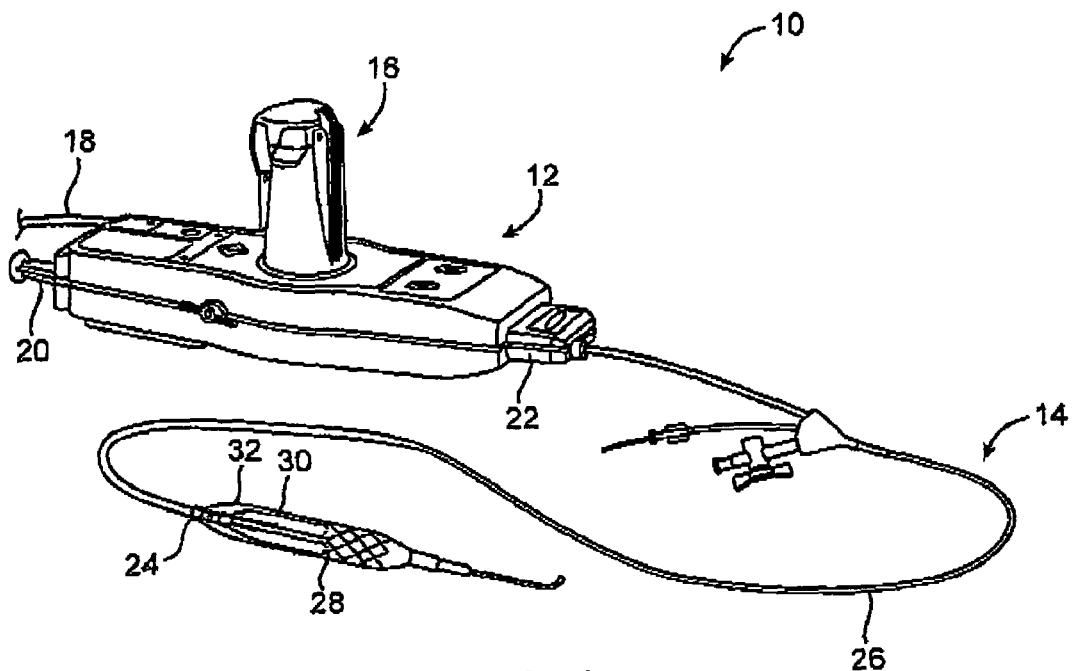
FIG. 1 is a perspective partial cutaway view of a cryogenic balloon catheter system according to the principles of the present invention.

Referring now to FIG. 1, a catheter system 10 generally includes a controlled/supply unit 12 and a catheter 14. Unit 12 includes a cooling fluid supply 16 along with cooling fluid control system components such as valves, pressure transducers, electronic controller hardware and/or software, and the like. Unit 12 may incorporate user interface capabilities including input keys, a display, and the like. Alternative embodiments may make use of external user interface or data processing structures, and the components of unit 12 may be separated into different housing structures.

The exemplary supply/control unit 12 includes a cable 18 for supplying electrical power from a battery, wall outlet, or other convenient power source. Acklitionally, a vacuum source 20 is integrated into unit 12 here in the form of a positive displacement pump such as a syringe. A housing of unit 12 has a size, shape, and weight suitable for holding in a single hand during a procedure. Unit 12 is coupled to catheter 14 by interfacing hubs or connectors 22 on the unit and catheter. Unit 12, catheter 14, and the interfacing connectors are more fully described in co-pending U.S. patent application Ser. No. 09/953,464 (now U.S. Pat. No. 6,648,679) filed on Sep. 14, 2001, and entitled "Improved Safety Cryotherapy Catheter," the full disclosure of which is incorporated herein by reference.

Catheter 14 generally has a proximal end adjacent connector 22, a distal end 24, and an elongate catheter body 26 extending therebetween. A balloon 28 is disposed adjacent distal end 24 of catheter body 26. In the exemplary embodiment, balloon 28 comprises an inner balloon 30 and an outer balloon 32 with a vacuum space (see FIG. 3). By monitoring a vacuum applied between the first and second balloons, and by shutting off the cooling fluid flow if the vacuum deteriorates, containment of both the first and second balloons can be effectively monitored and release of cooling liquid or gas within the vasculature can be inhibited.

Figure 2:
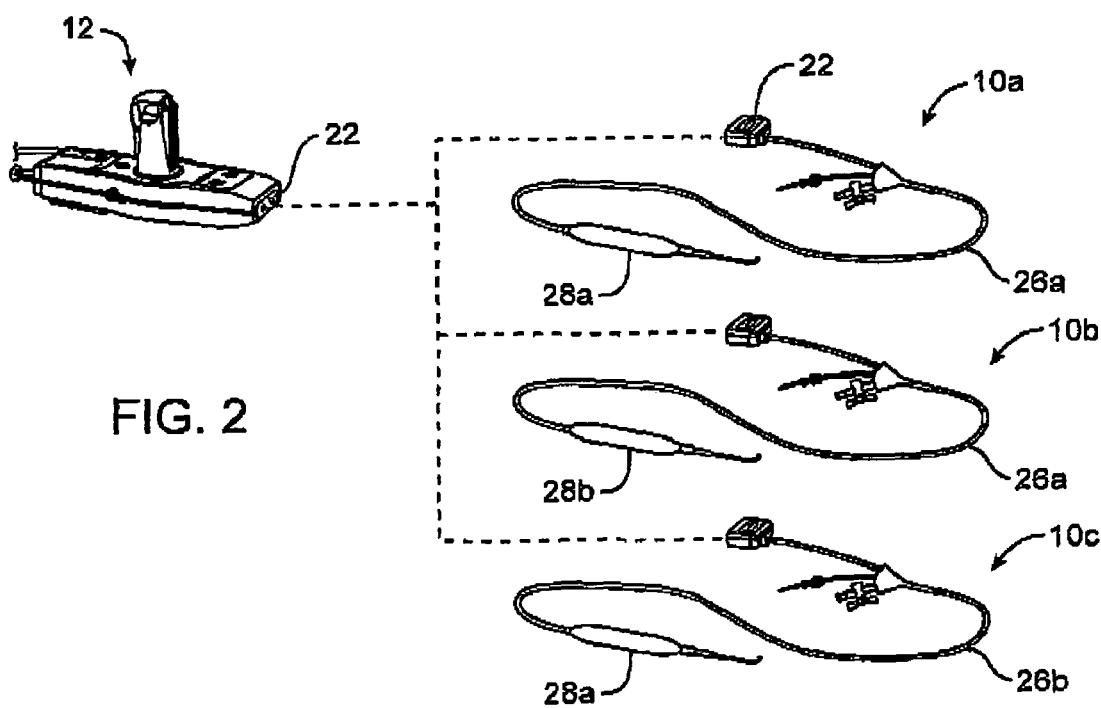
FIG. 2 schematically illustrates alternatively selectable coupling of a proximal housing of the balloon catheter system of FIG. 1 with any of plurality of differing cooling balloon catheters having differing cooling fluid flow characteristics.

Referring now to FIG. 2, during a cryogenically cooled balloon inflation, the inflation media may be maintained in a canister within unit 12 at a high pressure of over 650 psi, typically at between 850 and 950 psi. Use of a small sealed canister having a small volume provides a convenient single-use system which can avoid overtreatment do to exhaustion of the cooling fluid. Nitrous oxide canisters having volumes between 10 cc and 20 cc may contain between about 8 gms to about 25 gms of cooling fluid provide a very safe, effective cooling and inflation media for the balloon catheter system 10. However, balloon inflation rates when these high-pressure canisters are coupled to balloon catheter system 10 may be excessive, often being less than 0.1 seconds. Balloon inflations at these high rates can cause excessive damage to the vessel in the treatment area, and may result in higher dissection rates, higher restenosis rates, and the like.

A variety of control methodologies may be employed to reduce the balloon inflation rate. However, as illustrated in FIG. 2, unit 12 may be selectively coupled to any of a plurality of selectable balloon catheters 10$a$, 10$b$, 10$c$, . . . These balloon catheters will often have catheter bodies, balloons, and/or other components with significantly differing characteristics. As these differing characteristics will significantly impact the flow characteristics of the cooling fluid from unit 12, a control methodology providing a controlled inflation rate for any of the selected balloon catheters 10$a$, 10$b$, 10$c$, . . . when coupled to unit 12, is desirable.

Addressing the specific characteristics of the balloon catheters 10 illustrated in FIG. 2, a first balloon catheter 10$a$, has a first catheter body 26$a$ coupled to a first balloon 28$a$. A second catheter 10$b$ has a catheter body 26$a$ which is similar to that of the first catheter, but a balloon 28$b$ with a length (and hence volume) which is significantly larger than that of the first balloon. A third catheter 10$c$ has a catheter body 26$b$ which is significantly longer than first catheter 26$a$, and so forth. It will often be advantageous to provide more than five alternatively selectable catheters with differing flow characteristics, in many cases ten or more alternative selectable catheters, and preferably twenty or more alternatively selectable catheters. Catheters having a catheter body length of 90 cm or less will often be included with a set of alternatively selectable catheter along with one or more catheters having a catheter body length of over 100 cm. Balloon lengths (measured along an axis of catheter body 26) may be included in set with a balloon having a length of more than 5 cm. Similarly, balloon diameters of 5 or less mm may be included with balloon diameters of 6 mm or more.

In an exemplary set of alternatively selectable catheters, catheter body lengths of 80 and 120 cm may be provided, along with balloon lengths of 2, 4, and 6 cm. Some or all of the combinations of body lengths and balloon lengths may be available in catheters having balloons with diameters of 4, 5, 6, and 7 mm. The exemplary set includes 24 catheters having differing flow characteristics, which may result from additional differences between the catheter structures. For example, along with differing catheter lengths, balloon lengths, and balloon diameters, the orifice length for cooling of fluid entering the balloon may differ among the differing catheters (often as a function of balloon length, with longer balloons having shorter orifices so that the flow rate of cooling fluid will be sufficient to cool the entire balloon surface).

Significant variations between the catheters, the volume and diameter of the cooling fluid inflow lumens to the balloons, the temperature of the tubing transmitting the cooling fluid, the manifold coupling the supply canister to the catheter body, and other physical differences can significantly alter the temperature and/or gas/liquid mix of the nitrous oxide fluid entering the catheter. This can complicate pressure control algorithms, making it difficult to produce a uniform response in the widely varying catheters which might be selected. Furthermore, the response time of the entire cooling fluid system when measuring exhaust flow from the catheter body may make it difficult to rely on a simple feedback loop so as to produce, for example, uniform pressure steps throughout a range of catheters.

Referring now to FIGS. 3 and 4, a variety of the structures of catheter 10 are shown in more detail. Catheter body 26 includes a cooling fluid supply lumen 40 and an exhaust lumen 42 extending the proximal and distal ends of the catheter body. The first and second balloons 30, 32 may be integral extensions of the catheter body, or may be separately formed and attached thereto. The balloon may be formed from the same or different material as the catheter body and may be attached to the catheter body by adhesives, heat welding, or the like. Catheter body 26 may comprise a variety of polymer materials, including polyethylenes, polyimides, nylons, polyesters, and/or copolymers and derivatives thereof. Balloon 30, 32 may comprise elastic and/or inelastic structures, and may comprise material such as nylon, polyethyleneterephathalate (PET), urethane, latex, silicone, polyethylene, high strength polymers such as PEBAX™, and/or the like. Balloons 30, 32 may be formed from different materials, for example, the first balloon comprising a high-strength material such as PET, while the second balloon comprising a highly durable material such as polyethylene. Balloon 28 will typically have a length of at least 1 cm, preferably being in a range from about 1.5 cm to 10 cm, and may have diameters in a range from 1.5 mm to about 10 mm.

A thermal barrier may be disposed within vacuum space 34, the thermal barrier comprising or maintaining a gap between the balloons. Suitable thermal barriers may comprise woven, braided, helically wound, or knotted fibers such as polyester materials commercially available from SAATITECH of Summers, N.Y. under the SAATIFIL™ polyester, PES 38/31M. A radiopaque marker may also be disposed on the polyester layer, or otherwise between the first and second balloons so as to facilitate imaging. A wide variety of alternative structures are also possible, including the use of thermal barriers comprising fluids which change phase at a selected temperature, as more fully described in U.S. Pat. No. 6,648,679, previously incorporated herein by reference.

Still referring to FIGS. 3 and 4, a hub 44 along catheter body 26 may couple a guidewire port 46 to a guidewire lumen 48 of the catheter body. A balloon deflation port 50 is coupled to exhaust lumen 42 so as to facilitate deflation of the balloon after completion of a procedure. At least one rupture disk may disposed between the inner surface of the inner balloon and the vacuum space so as to shut down the system prior to a balloon burst. Vacuum space 34 may be coupled to hub 22 by vacuum lumen 52, while wire 54 couple sensors of the balloon to unit 12.

Figure 5:
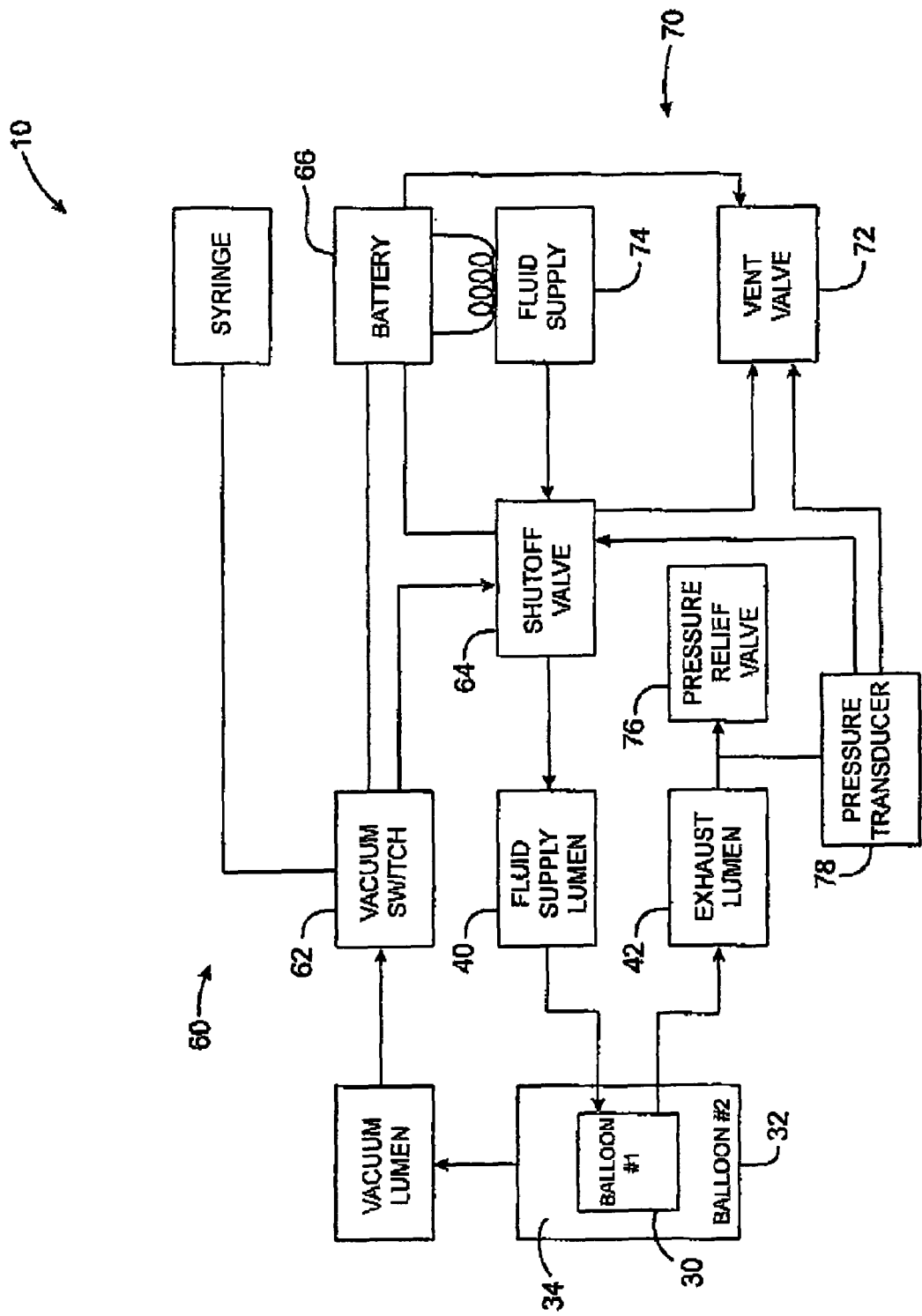
FIG. 5 is a functional block diagram illustrating components of the balloon catheter system of FIG. 1.

FIG. 5 illustrates a functional flow diagram of some of the fluid path and control components of system 10. A fluid shut-off portion 60 of system 10 generally includes a vacuum switch 62 connected to a shut-off valve 64 by a circuit, the circuit being powered by a battery 66. The switch 62 may remain closed only when a predetermined level of vacuum is detected. Alternatively, the circuit may be arranged so that the switch is open only when the predetermined vacuum is present, with the shut-off valve 64 being opened when the switch is open. The vacuum is reduced when there is a breach in the catheter body, inner balloon, and/or outer balloon, allowing cryogenic fluid or blood to enter the vacuum lumen or vacuum space.

In a pressure control portion 70 of the system, fluid flows along a cooling fluid path from a fluid supply 74 (such as a nitrous oxide canister) through a shut-off valve 64. When the delivery valve 64 is opened, fluid is allowed to advance along fluid supply lumen 40 to balloon 30, where at least a portion of the cooling fluid changes phase from a liquid to a gas. Some portion of the fluid may also change from a liquid to a gas prior to entry of balloon 30 and/or after the balloon is exhausted from balloon 30 into exhaust lumen 42. A pressure relief valve 76 controls release of the exhaust, typically to the surrounding environment. In alternative systems, the exhaust may be released to a vacuum source, a waste chamber, a recycling system, or the like. Relief valve 76 controls the back pressure in exhaust lumen 42 and balloon 30.

When shut-off or delivery valve 64 is opened, the cooling fluid from fluid supply 74 is allowed to advance to a vent valve 72. Then valve 72 (and other structures of the cooling fluid control portion 70) are coupled to battery 66. The coupling circuitry will often comprise a timer to establish a valve cycle time. When vent valve 72 is open, cooling fluid from the fluid supply and/or fluid supply lumen is vented, significantly limiting the flow of cooling fluid into balloon 30.

As explained in detailed below, a venting and/or shut-off valve cycle regimen may be selected in response to a measured pressure from transducer 78. Specifically, an initial or calibration cooling fluid flow may be introduced in the fluid supply 40 by opening and closing shut-off valve 64. By measuring the pressure at transducer 78, this allows the controller to determine at least some of the cooling fluid flow path characteristics for the system. In the exemplary embodiment, a valve cycle time for the vent valve and/or shut-off valve are determined in response to a pressure of the exhaust measured by pressure transducer 78. Once again, additional aspects of the functional block diagram for this system including the use of a heater powered by battery 66 to control a temperature of fluid supply 74 are described in more detail in co-pending U.S. patent application Ser. No. 09/953,464 (now U.S. Pat. No. 6,648,679) filed on Sep. 14, 2001, previously incorporated herein by reference.

Figure 6:
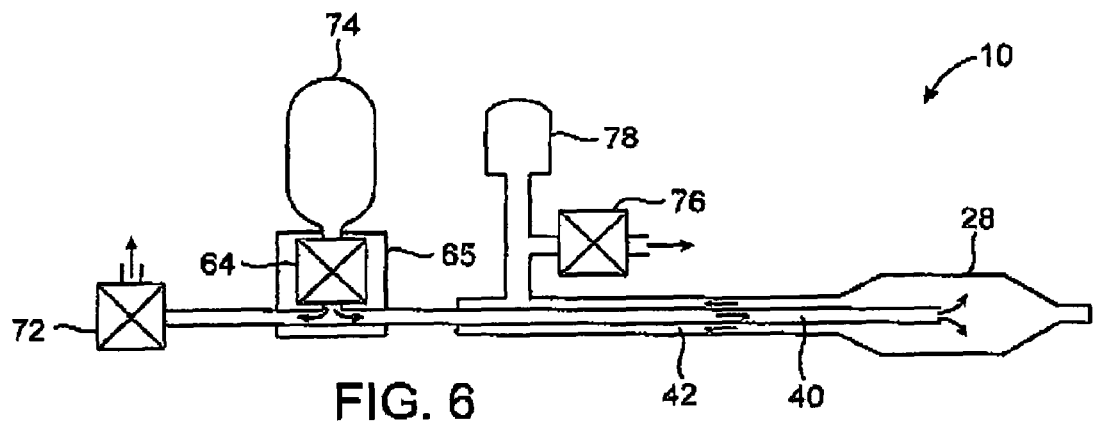
FIG. 6 is a schematic illustrating components disposed along the cooling fluid flow path of the system of FIG. 1

Components of system 10 along the cooling fluid flow path are illustrated in FIG. 6. A method 80 for using these components is illustrated in flow-chart form in FIG. 10.

Figure 10:
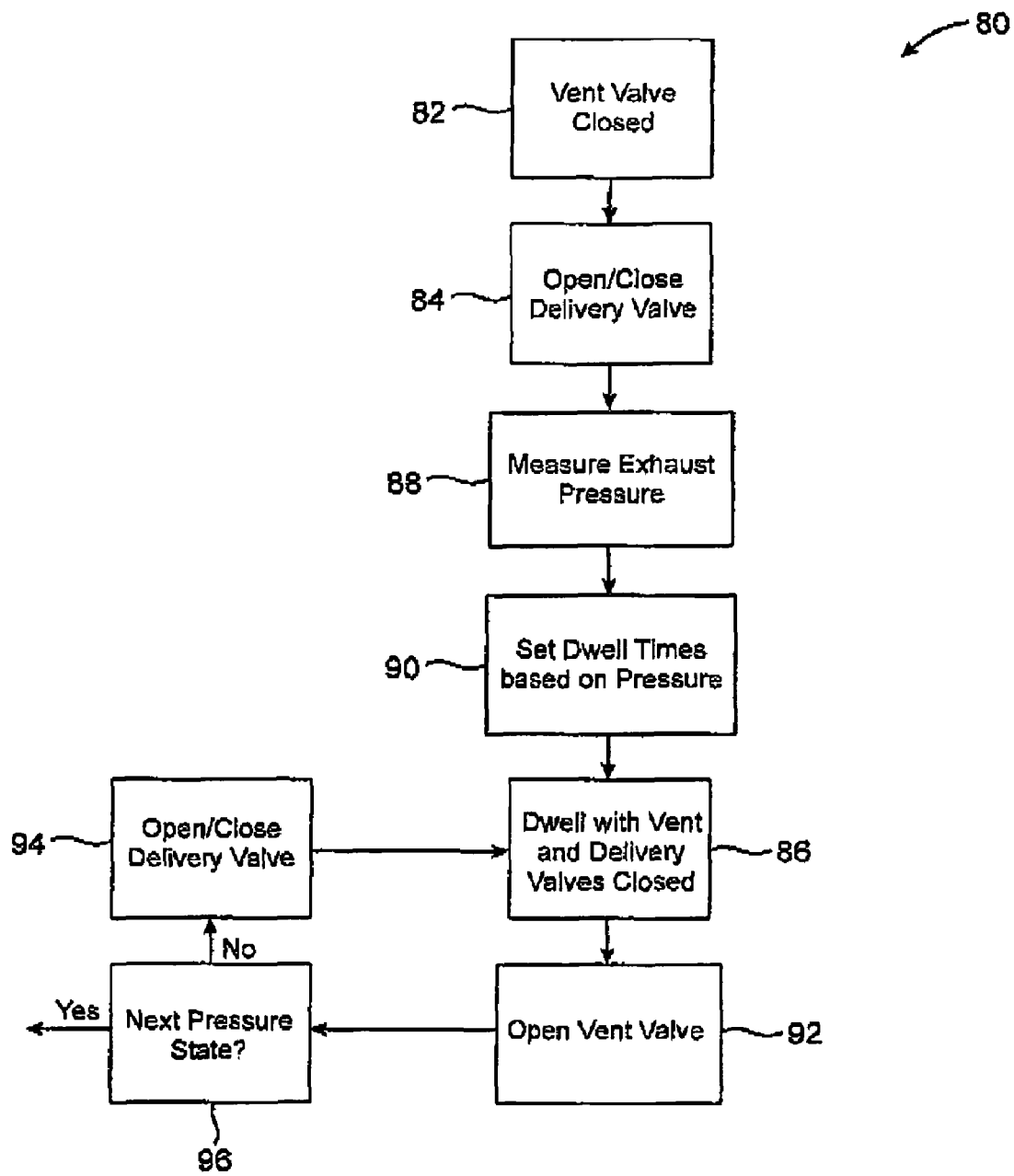
FIG. 10 is a flow chart of steps for inflating the balloon of the system of FIG. 1 to a desired pressure.

Referring to FIGS. 6 and 10, with the vent valve closed 82, the delivery or shut-off valve 64 is opened for a time sufficient to introduce cooling fluid into lumens of a supply lumen manifold 65. The vent valve may be open for less than half a second, ideally being open for 20 ms. The system will dwell with the vent and delivery valves both closed 86, and exhaust pressure can be measured by transducer 78 before, during, and/or after dwelling in this closed condition at step 88. Dwell times may be based on the measured pressure 90. While dwelling with the valves closed, the cooling fluid within the manifold 65 will boil so as to delivery cooling fluid (optionally as a gas/liquid mixture) to the balloon. After the dwell time, the vent valve 72 may be opened 92. Opening and closing at the delivery valve may be repeated 94, with repeated dwell times 86 so that the balloon will reach an intermediate pressure. Once the intermediate pressure has been achieved, the balloon may be stepped up to the next pressure state 96.

Preferably, a short initial dwell time 86 may be used to produce a pressure increase between approximately 5 and 25 psi. The measured pressure 88 from this step may be used to calculate the dwell or cycle times for subsequent valve cycles. In general, catheters having flow characteristics which result in relatively large measured exhaust pressures include catheters having long balloons with low volumes and room temperature manifolds. Short dwell times and valve cycle periods will appropriate to provide an intermediate pressure for such catheters. Catheters having low measured exhaust pressures will benefit from a longer dwell and valve cycle time in step 86 to achieve the desired intermediate pressure.

Figure 7:
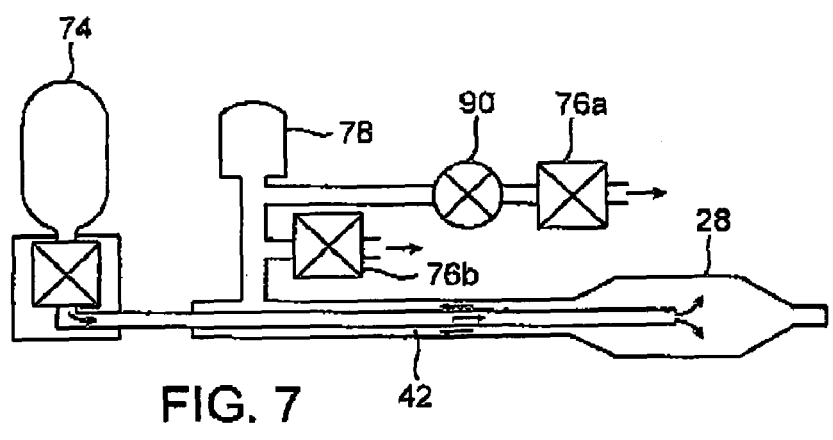
FIG. 7 schematically illustrates an alternative cooling fluid path and the associated components.

Referring now to FIG. 7, the use of cooling before and/or during dilation of a lesion may allow the use of dilation balloon inflation pressures which are lower than those typically applied for uncooled balloon angioplasty. In some embodiments, inflating balloon 28 at a pressure of about 8 atm and cooling the engaged vessel wall tissues to a temperature between about −2° C. and −12° C., ideally to −10° C., can open a stenotic lesion while inhibiting recoil and/or restenosis. Some lesions, particularly heavily calcified or fibrotic lesions, benefit from higher pressures. It may be advantageous to first dilate the lesion with a lower pressure so as to limit any damage to the vessel wall. If dilation of the vessel is not successfully at the lower pressure, a second higher pressure (optionally followed by a third even higher pressure) dilation may be desirable.

In the system of FIG. 7, balloon pressure may be largely controlled by a pressure relief valve 67a coupled to a pressure transducer 78. So as to allow the use of a higher selectable pressure, first and second pressure relief valves 76a and 76b are coupled to exhaust lumen 42. First pressure relief valve 76a may be set at a lower pressure (for example, approximately 8 atm or less to account for pressure drop of the gas along the catheter body) while the second pressure relief valve 76b is set at a somewhat higher pressure (for example, at 10 atm or slightly less). By manually turning a stopcock valve 90 to a closed position, the lower pressure relief valve 76a may be isolated from the exhaust system so that the catheter runs at the higher pressure. When the valve in the open position, gas will exhaust out of the lower pressure valve.

Figure 9:
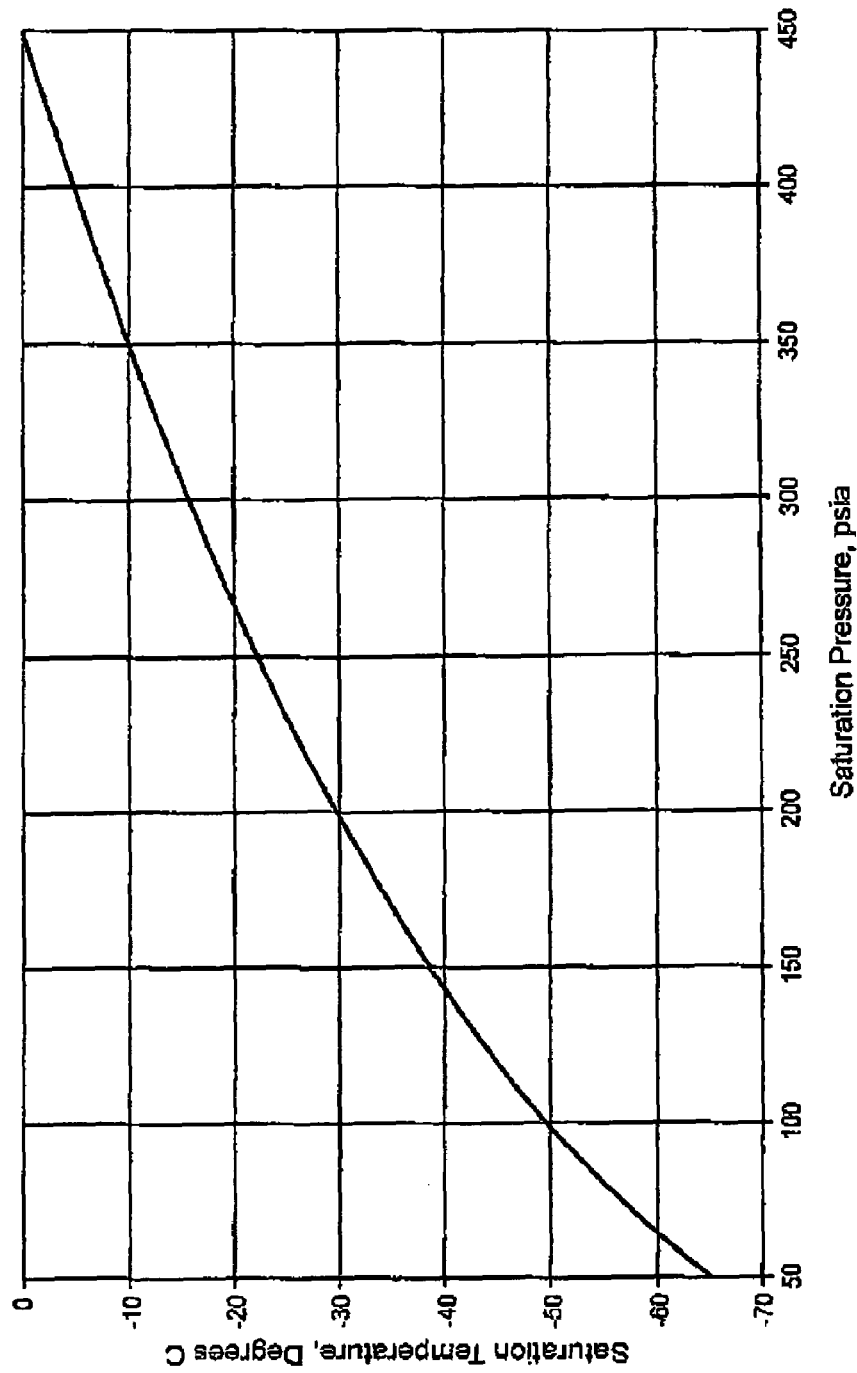
FIG. 9 graphically illustrates the coupling of inflation pressure and temperature for nitrous oxide, one inflation fluid for using the system of FIG. 1.

As can be understood with reference to FIG. 9, when the balloon operates at different pressures the cooling fluid (often nitrous oxide) inside the balloon will evaporate at a different temperature. At 8 atm, the temperature inside the balloon will be about −40° C. At 10 atm, the temperature inside the balloon may be about −35° C. so as to provide a target tissue temperature (often about −10° C.), the time for which cooling fluid flows may be adjusted so as to provide a longer cooling period for the higher pressure inflation than the lower pressure inflation. When using nitrous oxide at 8 and 10 atm, the time to reach the target temperature of −10° C. may be about 20 and 30 seconds, respectively. The pressure transducer may detect the exhaust pressure and signal the microprocessor of unit 12 to run the appropriate time for the balloon pressure selected.

Figure 8:
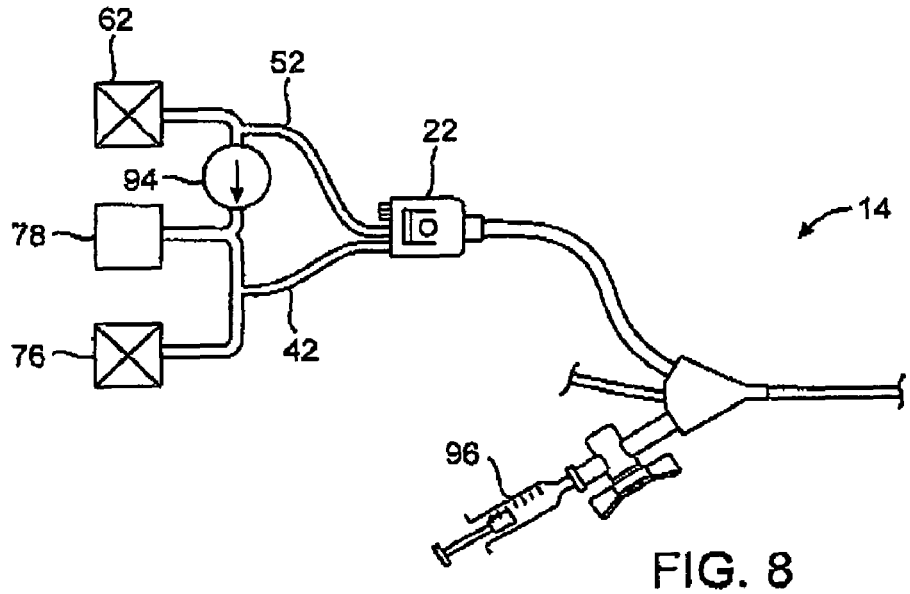
FIG. 8 schematically illustrates a vacuum system for deflating inner and outer balloon in the system of FIG. 1, and for establishing a vacuum for detecting leaks of the inner and outer balloons.

Referring now to FIG. 8, before catheter 14 is introduced into a vessel, a vacuum is normally applied to both the inner balloon 30 and the outer balloon 32 so as to minimize the catheter profile and activate the vacuum transducer. (see FIGS. 3 and 5) As vacuum space 34 and vacuum lumen 52 remain below ambient pressure during the procedure, it is beneficial to isolate the inner and outer vacuum circuits when the inner balloon is inflated. By including a one-way valve 94 between the vacuum lumen 52 and the exhaust lumen 42, and by drawing a vacuum in the exhaust lumen using a vacuum source 96, both balloons may be deflated simultaneously without having to rely on two separate vacuum sources.

Figure 11A:
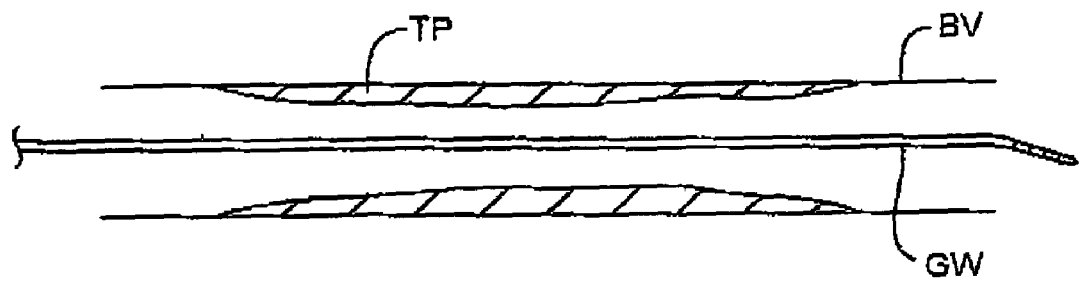
FIGS. 11A–11D are cross-sectional views schematically illustrating treatment of the blood vessel using the system of FIG. 1.
Figure 11B:
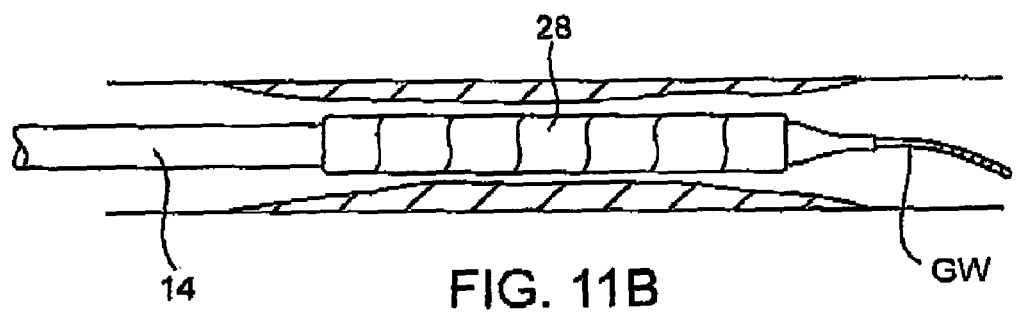
Figure 11C:
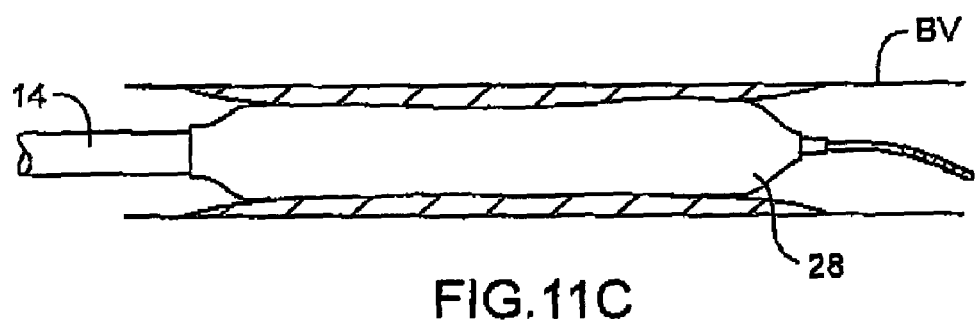
Figure 11D:
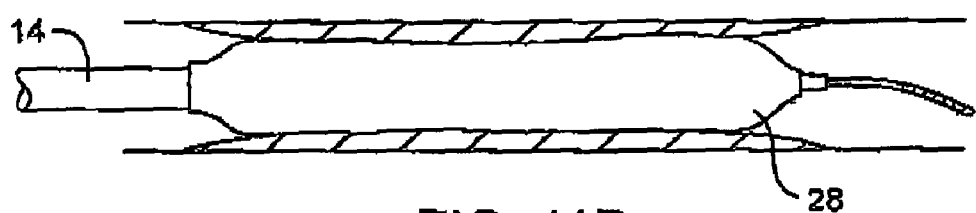

Referring now to FIGS. 11A to 11D, methods for treating a target portion TP of a blood vessel BV can be understood. Catheter 14 is introduced over a guidewire GW, so that balloon 28 is positioned within the blood vessel BV adjacent the target portion TP. An initial cooling fluid flow 11B or calibration cooling fluid flow may be introduced into the cooling fluid path so as to vaporize therein. This initial or calibration flow may result in an exhaust characteristic (such as exhaust pressure) which can be measured downstream of balloon 28, allowing the system to identify an appropriate cooling fluid flow regimen. Hence, an appropriate cooling fluid control algorithm may be applied to subsequent cooling fluid flows so as to provide an intermediate pressure state within balloon 28 as schematically illustrated in FIG. 11C. The controlled intermediate pressure state will often comprise an intermediate balloon pressure, but may also comprise a controlled rate of increase in the pressure. Such pressure increase rates may be defined as a series of pressure increase steps, typically being 3 or more pressure increase steps.

As illustrated in FIG. 11B, balloon 28 may reach a fully inflated state in a time from about 0.25 to about 10 seconds after beginning inflation, many times being 1 second or more, and often in a time from about 0.5 to about 7 seconds, and optionally being about 7 seconds or more. In some embodiments, particularly when the intermediate pressure comprises a first dilation pressure which is followed by a subsequent higher dilation pressure using the system of FIG. 7 or the like, significantly longer times may pass between initial inflation of the balloon and inflation to a maximum inflation pressure.

While the exemplary embodiments have been described in some detail, by way of example and for clarity of understanding, those of skill in the art will recognize that a variety of modification, adaptations, and changes may be employed. Hence, the scope of the present invention should be limited solely by the appending claims.

What is claimed is:

1. A method for treating a region of a blood vessel, the method comprising:
positioning a balloon of a balloon catheter within the blood vessel and adjacent the region while the balloon is in a first configuration;
cooling the region with the balloon in a second configuration by changing a cooling fluid from a liquid phase to a gas phase within the balloon so as to urge the balloon radially outwardly; and controlling an intermediate cooling fluid pressure state within the balloon while the balloon is between the first configuration and the second configuration, wherein the intermediate pressure state comprises a rate of change of pressure within the balloon between the first configuration and the second configuration.

2. The method of claim 1, wherein the control step results in an inflation time from the first configuration to the second configuration of 1.0 seconds or more.

3. The method of claim 1, wherein the rate of change of pressure is defined by a plurality of step increases in pressure within the balloon.

4. The method of claim 1, further comprising selecting the balloon catheter from among a plurality of differing alternative balloon catheters having differing cooling fluid flow characteristics, wherein the controlling step is performed so as to compensate for the alternative cooling fluid flow characteristics and provide the pressure change rate within a desired range.

5. The method of claim 1, wherein the intermediate state comprises an intermediate balloon pressure, the intermediate pressure being greater than a first configuration balloon pressure and less than a second configuration balloon pressure.

6. The method of claim 1, further comprising selecting the balloon catheter from among a plurality of differing alternative balloon catheters having differing alternative cooling fluid flow characteristics.

7. The method of claim 6, further comprising determining a cooling fluid valve control regimen in response to flow characteristics of the selected balloon catheter.

8. The method of claim 7, wherein the control regimen provides a balloon temperature within a desired temperature range, and wherein alternative different control regimens compensate for the different flow characteristics of the alternative balloon catheters.

9. The method of claim 6, further comprising determining the flow characteristics of the selected balloon catheter by introducing an initial cooling fluid flow into the selected balloon catheter, and by sensing an exhaust flow property of the initial fluid flow from the balloon catheter.

10. A method for treating a region of a blood vessel, the method comprising:

positioning a balloon of a balloon catheter within the blood vessel and adjacent the region while the balloon is in a first configuration;

cooling the region with the balloon in a second configuration by changing a cooling fluid from a liquid phase to a gas phase within the balloon so as to urge the balloon radially outwardly;

controlling an intermediate cooling fluid pressure state within the balloon while the balloon is between the first configuration and the second configuration; and coupling a fluid supply to a supply lumen of the balloon catheter so as to provide a fluidpath extending from the fluid supply, distally along the supply lumen, into the balloon, and proximally along an exhaust lumen of the balloon catheter, wherein the pressure controlling step comprises venting of at least a portion of the cooling fluid upstream of the balloon.

11. The method of claim 10, wherein the pressure controlling step further comprises periodic opening and closing of a vent valve coupled to the fluid path upstream of the balloon.

12. The method of claim 11, wherein the pressure controlling step further comprises periodic opening and closing of a fluid delivery valve disposed along the fluid path between the fluid supply and the balloon.

13. The method of claim 12, wherein the cooling fluid comprises nitrous oxide, wherein the vent valve opens and closes according to a valve cycle time, wherein the fluid delivery valve opens and closes according to the valve cycle time, and wherein the vent valve is open for longer portion of the valve cycle time than the fluid delivery valve.

14. The method of claim 10, further comprising sensing a pressure along the fluid path downstream of the balloon and determining the venting of the cooling fluid in response to the pressure.

15. A method for cooling a region of a blood vessel to a predetermined cooling temperature, the method comprising:

positioning a balloon of a balloon catheter system within the blood vessel and adjacent the region while the balloon is in a first configuration;

selecting a balloon inflation pressure by selecting between a first pressure relief valve and a second pressure relief valve downstream of the balloon along the cooling fluid path, the first and second values both being coupled to the balloon catheter;

inflating the balloon by changing a cooling fluid from a liquid phase to a gas phase along a cooling fluid path of the balloon catheter system; and controlling cooling fluid flow along the cooling fluid path so as to provide the selected balloon inflation pressure and the predetermined cooling temperature.

16. A catheter system for cooling a region of a blood vessel, the system comprising:

a balloon catheter having a catheter body with a proximal end, a distal end, and a balloon disposed near the distal end, the catheter body having a supply lumen and an exhaust lumen in fluid communication with the balloon;

a fluid supply coupleable to the proximal end of the catheter body so as to define a cooling fluid path extending distally along the supply lumen, through the balloon, and returning proximally along the exhaust lumen, the fluid supply having a cooling fluid which changes phase from a liquid to a gas so as to effect cooling; and a cooling fluid control system coupled to the fluid path, the fluid control system having at least one of controller software or controller hardware configured to implement a first configuration in which the balloon is uninflated, a second configuration in which the balloon is inflated to a treatment pressure and cools the region to a treatment temperature, and an intermediate configuration in which an intermediate pressure state of the balloon is controlled, wherein the intermediate pressure state comprises a rate of change of balloon inflation pressure.

17. The catheter system of claim 16, wherein the intermediate pressure state comprises a lower pressure than the treatment pressure.

18. The catheter system of claim 16, wherein the pressure change rate is such that inflation of the balloon from the first configuration to the second configuration is at least about 0.25 seconds.

19. The catheter system of claim 18, wherein the cooling fluid comprises nitrous oxide, and wherein the treatment pressure is in a range from about 7 to about 11 atm.

20. The catheter system of claim 18, wherein the pressure change rate of the controller software or controller hardware is defined by a plurality of increasing pressure steps.

21. The catheter system of claim 16, further comprising a plurality of alternatively selectable balloon catheters having differing cooling fluid flow characteristics, each alternative balloon catheter being coupleable to the fluid supply so as to define an associated alternative fluid path, wherein the controller software or controller hardware of the fluid control system is configured to compensate for the differing flow characteristics so as to provide at least one of a treatment temperature in a desired temperature range, a treatment pressure in a desired treatment pressure range, and a pressure change rate in a desired pressure change rate range.

22. The catheter system of claim 16, wherein the flow control system comprises a vent valve disposed along the cooling fluid path upstream of the balloon.

23. The catheter system of claim 18, further comprising a timer adapted for periodically cycling the vent valve open and closed.

24. The catheter system of claim 22, wherein the flow control system further comprises a fluid delivery valve disposed between the fluid supply and the balloon.

25. The catheter system of claim 24, wherein the cooling fluid comprises nitrous oxide, further comprising a timer periodically cycling the vent valve open and closed with a cycle time period, the timer periodically cycling the fluid delivery valve open and closed with the cycle time period, the vent valve being open for a larger portion of the cycle time period than the fluid delivery valve.

26. The catheter system of claim 16, wherein controller software or controller hardware of the flow control system is configured to introduce an initial cooling fluid flow and determines an appropriate cooling flow regime in response to characteristic of the initial flow downstream of the balloon.

27. The catheter system of claim 26, wherein the cooling flow regime comprises a valve cycle period, and wherein the downstream characteristic comprises an exhaust pressure.

28. The catheter system of claim 16, wherein the flow control system comprises alternative selectable pressure relief valves downstream of the balloon.

29. A catheter system for cooling a region of a blood vessel, the system comprising:
first and second alternatively selectable balloon catheters, each balloon catheter having a catheter body with a proximal end, a distal end, and a balloon disposed near the distal end, the catheter body having a supply lumen and an exhaust lumen in fluid communication with the balloon;
a fluid supply selectably coupleable to the proximal end of each catheter body so as to define a cooling fluid path associated with the selected balloon catheter, the fluid supply having a cooling fluid which changes phase from a liquid to a gas so as to effect cooling, a characteristic of a first cooling fluid path associated with the first balloon catheter differing significantly from that of a second cooling fluid path associated with the second balloon catheter; and
a cooling fluid control system coupled to the fluid path, the fluid control system having a sensor coupled to the fluid flow path, the sensor generating a calibration signal in response to a calibration fluid flow from the supply in a calibration mode, the fluid control system comprising at least one of electronic controller hardware and electronic controller software configured to control balloon pressure based at least in part on the calibration signal in a treatment mode.

30. A method for treating a region of a blood vessel, the method comprising:
positioning a balloon of a balloon catheter within the blood vessel and adjacent the region while the balloon is in a first configuration;
cooling the region with the balloon in a second configuration by changing a cooling fluid from a liquid phase to a gas phase within the balloon so as to urge the balloon radially outwardly;
controlling an intermediate cooling fluid pressure state within the balloon while the balloon is between the first configuration and the second configuration;
coupling a fluid supply to a supply lumen of the balloon catheter so as to provide a fluid path extending from the fluid supply, distally along the supply lumen, into the balloon, and proximally along an exhaust lumen of the balloon catheter, wherein the pressure controlling step comprises:
venting of at least a portion of the cooling fluid upstream of the balloon
periodic opening and closing of a vent valve coupled to the fluid path upstream of the balloon; and
periodic opening and closing of a fluid delivery valve disposed along the fluid path between the fluid supply and the balloon;
the vent valve opening and closing according to a valve cycle time, the fluid delivery valve opening and closing according to the valve cycle time, and wherein the vent valve is open for longer portion of the valve cycle time than the fluid delivery valve.

31. A method for treating a region of a blood vessel, the method comprising:
selecting a balloon catheter from among a plurality of differing alternative balloon catheters having differing alternative cooling fluid flow characteristics;
positioning a balloon of the balloon catheter within the blood vessel and adjacent the region while the balloon is in a first configuration;
determining the flow characteristics of the selected balloon catheter by introducing an initial cooling fluid flow into the selected balloon catheter, and by sensing an exhaust flow property of the initial fluid flow from the balloon catheter;
cooling the region with the balloon in a second configuration by changing a cooling fluid from a liquid phase to a gas phase within the balloon so as to urge the balloon radially outwardly; and
controlling an intermediate cooling fluid pressure state within the balloon while the balloon is between the first configuration and the second configuration.

* * * * *

UNITED STATES PATENT AND TRADEMARK OFFICE
CERTIFICATE OF CORRECTION

| | | |
|---|---|---|
| PATENT NO. | : 7,060,062 B2 | Page 1 of 1 |
| APPLICATION NO. | : 10/455253 | |
| DATED | : June 13, 2006 | |
| INVENTOR(S) | : Joye et al. | |

It is certified that error appears in the above-identified patent and that said Letters Patent is hereby corrected as shown below:

In the Claims:

Column 13, Line 18, Claim 23, delete "18" and insert --22--.

Signed and Sealed this
Thirtieth Day of April, 2013

Teresa Stanek Rea
*Acting Director of the United States Patent and Trademark Office*